United States Patent [19]
Saxon

[11] Patent Number: 5,743,917
[45] Date of Patent: *Apr. 28, 1998

[54] PROSTHESIS FOR THE REPAIR OF SOFT TISSUE DEFECTS

[76] Inventor: Allen Saxon, 57 Overbrook Rd., Barrington, Ill. 60010

[*] Notice: The term of this patent shall not extend beyond the expiration date of Pat. No. 5,725,577.

[21] Appl. No.: 295,028

[22] Filed: Aug. 25, 1994

Related U.S. Application Data

[63] Continuation-in-part of Ser. No. 24,233, Mar. 1, 1993, which is a continuation of Ser. No. 2,394, Jan. 13, 1993, abandoned.

[51] Int. Cl.$^6$ ............................................. A61F 2/08
[52] U.S. Cl. ............................ 623/11; 428/247; 427/2; 600/37; 606/151; 128/898
[58] Field of Search ............................ 623/1, 11, 12, 623/13; 427/424; 600/37; 606/151; 604/11, 13, 264

[56] References Cited

U.S. PATENT DOCUMENTS

| | | | |
|---|---|---|---|
| 4,693,720 | 9/1987 | Schamberg et al. | 623/11 |
| 4,769,038 | 9/1988 | Bendavid et al. | 623/13 |
| 5,433,996 | 7/1995 | Kranzler et al. | 428/247 |

FOREIGN PATENT DOCUMENTS 9009763  9/1990  WIPO.

*Primary Examiner*—David Isabella
*Attorney, Agent, or Firm*—Foley & Lardner

[57] ABSTRACT

A prothesis for the repair of soft tissue defects is provided. The prosthesis is made of a first portion comprising a first material which substantially does not incorporate into the host tissue and a second portion comprised of a second material which substantially incorporates into the host tissue, or which increases the structural integrity of the prosthesis, or which does both. A process for repairing a soft tissue defect by surgically implanting the prosthesis is also provided.

12 Claims, 8 Drawing Sheets

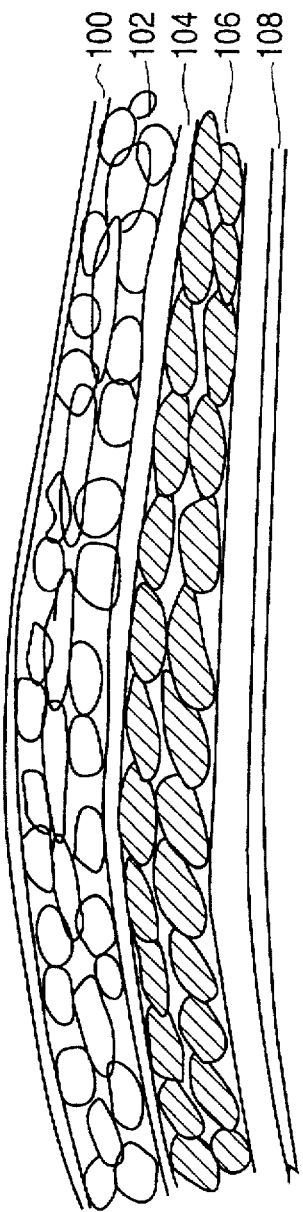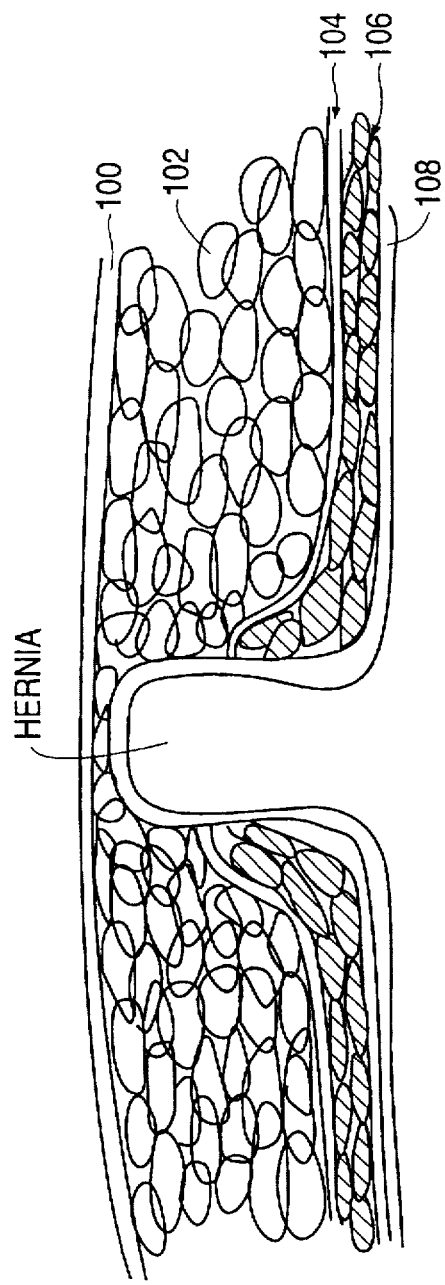

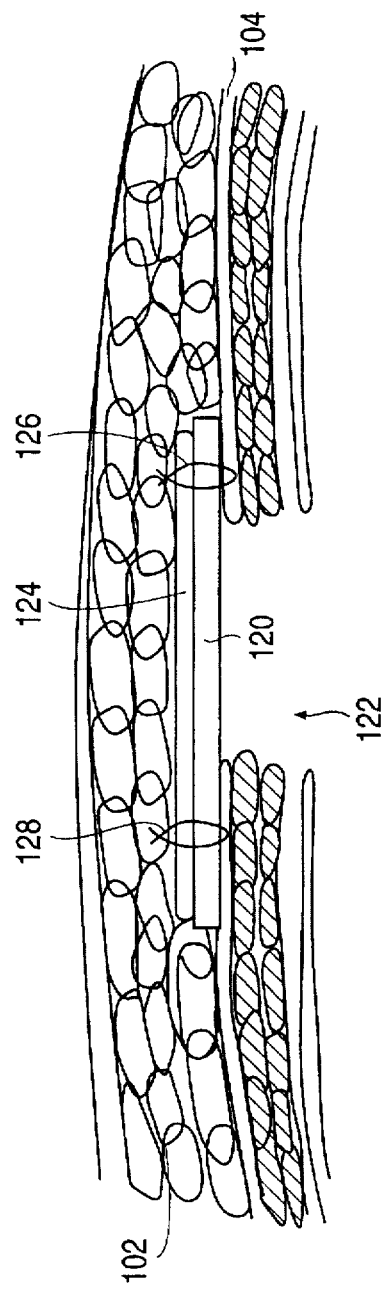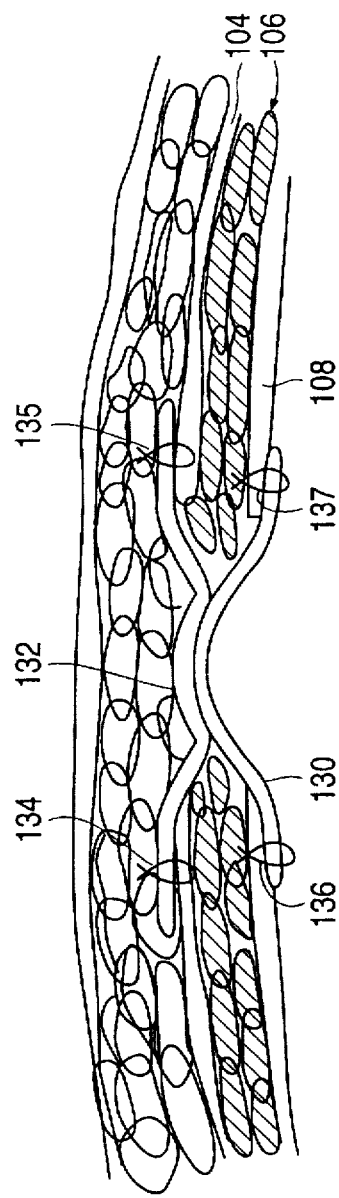

PROSTHESIS FOR THE REPAIR OF SOFT TISSUE DEFECTS

CROSS-REFERENCE TO RELATED APPLICATION

This application claims benefit under 35 U. S. C. §120 is a continuation-in part of U.S. application Ser. No. 08/024,233 filed Mar. 1, 1993, a continuation of application Ser. No. 08/002,394, filed Jan. 13, 1993, now abandoned.

FIELD OF THE INVENTION

This invention relates to a prosthesis for the repair of soft tissue defects, and to methods for repairing such defects.

BACKGROUND OF THE INVENTION

Soft tissue defects are defects in the soft tissue of an animal or human patient which lead to the formation of an opening in the tissue. They can occur, for example, in a hernia or as the result of extirpative tumor surgery. Such defects can be repaired by closing the opening formed from the defect by suturing, or by "patching" the opening with a prosthesis.

One of the most common soft tissue defects is an abdominal hernia. A hernia is an abnormal opening in the abdominal wall. A normal abdominal wall consists of layers of skin, fat, fascia, muscle and peritoneum. Hernias occur when there is a defect in the wall, and become significant when abdominal viscera (i.e., intestines or other internal organs) protrude through the defect, causing pain and presenting the danger of strangulation. A conventional procedure to repair a hernia utilizes sutures to close the opening and restore the integrity of the abdominal wall. Often, however, the fascial tissues involved have been weakened to the point that they will not maintain a repair if simply sutured together.

The repair of a large incisional hernia, particularly one which occurs in tissues weakened by previous surgery or in tissues of obese patients, remains a formidable task in general surgery. Factors such as obesity, chronic pulmonary disease, prior surgery, wound infection and seroma or hematoma formation continue to exert adverse influences on wound healing and increase the chance of recurrent herniation. Often, the abdominal wall tissues of these patients are severely compromised and weakened such that they will not support a primary repair, and any such closure may be associated with a significant recurrence rate.

Studies on the natural history of incisional hernias demonstrate an incidence of from 0.5% to 13.9% occurring following abdominal surgery. See, for example, Mc Vay et al., *Hernia*, Charles C. Thomas, ed., pp. 33–38, 1954; Blaustedt et al., *Acta Chir. Scand.*, 138: 275 (1972). In addition, long term studies have demonstrated a significant chance of the appearance of an incisional hernia long after the original surgery. See, for example, Mudge et al., *Br. J. Surg.*, 72: 70–71 (1985). The high failure rate following standard surgical suture repairs of incisional hernias has been discussed by many authors with recurrence rates as high as between 40% to 50%. See, for example, Langer et al., *Acta Chir. Scand.*, 151: 217–219 (1985); George et al., *Ann. R. Coll. Surg.*, 68(4): 185–187 (1986).

To reduce the chance of hernia recurrence and to allow for more satisfactory closure of the abdominal wall, the insertion of a prosthetic material may be required to accomplish the hernia repair. Several prosthetic materials have been proposed and are available for use as a substitute for the patient's tissue. These materials have different biological properties and have various advantages and disadvantages associated with them.

Both absorbable and nonabsorbable synthetic materials are available commercially for use in hernia repairs. Absorbable meshes (polyglycolic acid or polyglactin) disintegrate, and thus will not maintain a hernia repair. Nonabsorbable materials, however, are useful, and include tantalum mesh, stainless steel mesh, polyester cloth, polyester sheeting, polymeric meshes (e.g., MARLEX® and SURGI-PRO®) as polypropylene mesh, dacron mesh and nylon mesh, polyvinyl sponge, acrylic cloth, and expanded polytetrafluoroethylene (PTFE) (e.g., GORE-TEX®).

Two of the more readily available products are expanded PTFE and polypropylene mesh. These materials have been used independently in hernia repair. See, for example, Bauer et al., *Am. Surg.*, 206: 765–769 (1987); Usher et al., *Arch. Surg.*, 78: 138–145 (1959). They have different properties with regard to their degree of "incorporation," i.e., their fixation, into the host tissue.

Expanded PTFE is described in U.S. Pat. No. 4,187,390, and it is available from W. L. Gore & Associates, Inc. under the trade name GORE-TEX®. It can be obtained as a sheet of material which may be sutured in place over the soft tissue defect. Expanded PTFE substantially does not "incorporate" into the host tissues. That is, the tissues of a patient, over time, may incorporate somewhat into expanded PTFE, but this response is different from, and has a lesser degree of fixation than, that response which is observed with other materials, such as polypropylene mesh. This feature is a disadvantage when long-term fixation is desired, but represents a distinct advantage when exposed viscera such as intestines or other internal organs will come into contact with the material used in the soft tissue repair. That is, while other repair materials have been reported to cause major injury to abdominal viscera because the viscera incorporate into the repair material, the lesser degree of incorporation of expanded PTFE prevents such injuries. While there have been some reports that PTFE can adhere to viscera, there have been no reports of significant injury to viscera as a result of such incorporation.

Because it is a soft material, expanded PTFE may, when sutured in place, bulge somewhat and thereby provide a less than desirable cosmetic effect. Additionally, its poor ability to incorporate into the host's tissue may result in retraction or wrinkling and curling of the material if its lateral fixation, i.e., fixation by sutures, breaks loose or is disrupted.

The other commonly-used repair material, polypropylene mesh, is described in U.S. Pat. No. 4,769,038, and is available from C. R. Bard, Inc. under the trade name MARLEX®. The polypropylene mesh substantially incorporates itself into the patient's tissue, thereby fixing itself securely in place. Although this provides excellent long-term placement in the fascia and may protect against recurrent herniation over time, the substantial tissue incorporation may result in severe injury to any viscera which inadvertently may come in close contact with it for a prolonged period of time. Scattered reports of viscera injury exist and many surgeons have anecdotal evidence of the potential harm created in such situations. See, for example, Schneider et. al., *Am. Surg.* 45: 337–339 (1979). In one instance, a patient developed a small bowel fistula through polypropylene mesh one year following an otherwise unremarkable ventral hernia repair.

Thus, the currently available prosthesis, while providing some needed properties, present certain inherent disadvantages. That is, there is no prosthesis available which will both (i) lessen the likelihood of viscera injury by providing a surface which substantially does not incorporate into the host tissue and (ii) improve the incorporation of the prosthesis into the host by providing a surface which substantially incorporates into host tissue and/or which increases the structural integrity of the prosthesis by providing a component which increases the structural integrity. Thus, there is a continuing need for a prosthesis which will accomplish the foregoing objectives.

SUMMARY OF THE INVENTION

Accordingly, it is the object of the present invention to provide a prosthesis for repairing a soft tissue defect.

It is a further object of the present invention to provide a process for repairing a soft tissue defect.

Thus, a prothesis for the repair of soft tissue defects is provided. The prosthesis comprises a first portion comprised of a first material which substantially does not incorporate into the host tissue and a second portion comprised of a second material which substantially incorporates into the host tissue or which increases the structural integrity of the prosthesis, or which does both.

In one embodiment, the first and second portions are arranged to form layers, whereas in another embodiment, the first and second portions form a single layer.

In other embodiments, the first and second portions are substantially not joined together. In yet other embodiments, the first and second portions are at least partially joined together, e.g., by sutures, hemoclips and/or bonding.

In other embodiments, the first and second portions are of the same or different areas.

Yet other advantageous embodiments of the prosthesis are described.

Also provided is a process for repairing a soft tissue defect of a patient by surgically implanting any prosthesis of this invention adjacent the soft tissue defect. In one embodiment of the process, the first and second portions are both surgically attached to the fascia, whereas in another embodiment, the second portion is surgically attached to the fascia while the first portion is surgically attached to the peritoneum.

Additional objects and advantages of the present invention will be set forth in part in the description that follows, and in part will be obvious from the description, or may be learned by practice of the invention. The objects and advantages may be realized and obtained by means of the processes and compositions particularly pointed out in the appended claims.

BRIEF DESCRIPTION OF THE DRAWINGS

FIG. 10 is a view in cross-section of the normal anatomy of the abdominal wall;

FIG. 11 is a view in cross-section of an abdominal wall hernia;

FIG. 12 is a view in cross-section of an abdominal wall that has been repaired using a prosthesis of this invention, wherein the first and second portions are arranged in layers and are sutured to the fascia;

FIG. 13 is a view in cross-section of an abdominal wall that has been repaired using a prosthesis of this invention, wherein the first and second portions are arranged in layers and wherein the second portion is sutured to the fascia and the first portion is sutured to the peritoneum;

DETAILED DESCRIPTION OF THE PREFERRED EMBODIMENTS

Figure 1:
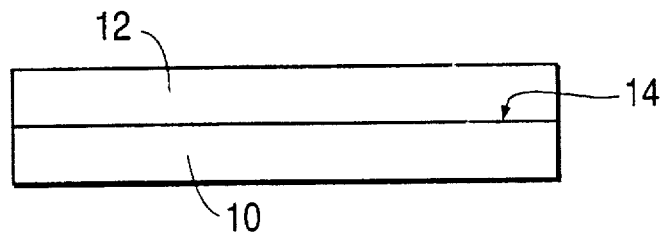
FIG. 1 is a side view in cross-section of an embodiment of a prosthesis in accordance with this invention.

The prosthesis of the present invention is suitable for use in the repair of soft tissue defects, such as soft tissue defects resulting from incisional hernias and soft tissue defects resulting from extirpative tumor surgery. It is also suitable for use in cancer surgeries, for example, in surgeries involving sarcoma of the extremities where saving a limb is a goal. Other applications of the prosthesis of the present invention include laparoscopic inguinal hernia repair, standard inguinal hernia repair, umbilical hernia repair, paracolostomy hernia repair, femora hernia repair, lumbar hernia repair, and the repair of other abdominal wall defects, thoracic wall defects and diaphragmatic hernias and defects.

The prosthesis of the present invention comprises a first portion comprising a first material which substantially does not incorporate into the host tissue, and a second portion comprising a second material which substantially incorporates into the host tissue, or which increases the structural integrity of the prosthesis, or which does both.

By the phrase "substantially does not incorporate into the host tissue," it is meant that the first portion will exhibit the type of incorporation generally observed with repairs using expanded PTFE. That is, while there is some tissue growth onto the prosthesis over time, such growth is of the type which generally does not result in damage to viscera. Typically, such growth may be characterized by formation of a "capsule" or band, which is adhered to the surface of the PTFE, but which is not substantially irreversibly fixed to it. A capsule is a smooth, uniform type of scar tissue which is generally easy to break up and/or remove from the expanded PTFE surface.

The observation that expanded PTFE substantially does not incorporate is consistent with the structure of expanded PTFE, which is an imporous material when viewed with the naked eye. There are no visible apertures for the tissue to grow through and form a substantial incorporation. While not wishing to be bound by any theory, it is believed that the expanded PTFE substantially does not incorporate into host tissue because its surface does not facilitate as substantial a fibroblastic reaction in the host tissue. Thus, one acceptable first material is expanded PTFE. This is available from W.L. Gore & Associates under the name GORE-TEX® (see U.S. Pat. No. 4,187,390). While some incorporation into host tissue may be observed with this material, no reports of significant injury to viscera as a result of this attachment have been reported. Thus, for the purpose of this invention, expanded PTFE substantially does not incorporate into host tissue. Those skilled in the art may recognize other suitable first materials.

The second material is one which substantially incorporates into the host tissue, or which increases the structural integrity of the prosthesis, or which does both. By "substantially incorporates into the host tissue," it is meant that, over time, the host tissue will grow substantially onto or substantially attach itself to the second material. Substantial incorporation is the type that is generally observed with repairs using polypropylene mesh. That is, with time the patient's fibrous and collagenous tissue substantially completely overgrow the mesh, growing through the openings therein and firmly affixing the mesh to the tissue. Eventually, it becomes difficult to recognize where the patient's tissue stops and the mesh begins. Such incorporation is consistent with the structure of the mesh, which has an array of apertures visible to the naked eye, through which the tissue can grow to achieve substantial fixation. Again, not wishing to be bound by any theory, it is believed that the polypropylene mesh, in contrast to the expanded PTFE, substantially incorporates into the host tissue because it facilitates a substantial fibroblastic reaction in the host tissue.

The skilled artisan who is familiar with surgical repair of tissue defects using a prosthesis readily will appreciate the meaning of the phrases "substantially does not incorporate" and "substantially incorporates" and their relative differences in type and degree of fixation to the patient's tissues.

Alternatively, the second material can increase the structural integrity of the prosthesis by reducing the effects of bulging, wrinkling and curling which may be associated with the first material. Suitable second materials may both substantially incorporate into the host tissue and increase the structural integrity of the prosthesis. Examples of suitable second materials include polypropylene mesh, prolene mesh, or mersilene mesh.

As mentioned, one acceptable second material is a polypropylene mesh, which is available from C. R. Bard, Inc. under the trade name MARLEX® (see U.S. Pat. No. 4,769,038). MARLEX® is one of the most commonly used materials in the repair of hernias because it incorporates rapidly into the host tissue and provides structural integrity to the prosthesis such that bulging, wrinkling and curling are not observed.

The two portions may be arranged to form more than one layer or substantially one layer, or the portions may be integrally formed. For example, the portions may be arranged in two layers, wherein one portion is on top of the other portion. Alternatively, the portions may be arranged in substantially one layer, wherein the portions are adjacent each other, for example, wherein the second portion substantially surrounds the first portion. In this way, a prosthesis could be made such that the first portion substantially covers any opening created by the soft tissue defect, and the second portion facilitates surgical attachment to, and incorporation into, the host tissue. Also contemplated is an arrangement wherein the two portions are integrally formed.

Alternatively, multiple layers of each material is also possible, either together or separated by one or more layers of another material, e.g., two first portions with a second portion therebetween. Optionally, additional layers which provide advantageous properties may be added. For example, an additional layer which enhances the overall resistance to bulging and/or which substantially incorporates into the host tissue may be added. Also, a layer comprising a material or composition (including, e.g., a gel) which completely absorbs into the host tissue or dissolves may be added. The skilled artisan will realize yet other combinations and permutations in which the first and second portions, either alone or with other layers, can be arranged to accomplish the objectives of this invention.

The two portions independently may be of any shape or size suited to fit the particular soft tissue defect. Examples of suitable shapes include circles, ovals, rectangles, squares and irregular shapes. The two portions may be of essentially the same dimensions or of different dimensions, such that one portion is larger than the other portion.

The portions may be separate, i.e., not joined together. Alternatively, they may be partially or substantially entirely joined together. Joining can be achieved by mechanical methods, such as by suturing or by the use of metal clips, for example, hemoclips, or by other methods, such as chemical or thermal bonding.

One advantageous embodiment provides a first portion of expanded PTFE (e.g., GORE-TEX®) which substantially entirely covers the soft tissue defect and a second portion of polypropylene mesh (e.g., MARLEX®) which facilitates incorporation into the host tissue. Such design combines the benefits associated with the mesh and the expanded PTFE while minimizing the drawbacks encountered when each is used separately. The expanded PTFE portion protects any underlying tissue, for example, viscera, which may come in contact with the prosthesis from being incorporated into the prosthesis. This prevents the severe injuries which may occur if internal organs, for example, small intestines, are inadvertently exposed to and subsequently incorporate into the polymeric mesh portion. The polymeric mesh portion provides additional structural integrity to the prosthesis, preventing the undesirable effects of bulging associated with prostheses which are comprised primarily of expanded PTFE. The polymeric mesh portion also substantially incorporates into the patient's tissue. This incorporation occurs rapidly, and provides secure, long-term fixation of the prosthesis into the host tissue. Moreover, when the two portions are joined together, the strength of the polymeric mesh portion will minimize the wrinkling and curling that may occur over time with the expanded PTFE portion.

The prosthesis of this invention is implanted into the patient using standard surgical techniques such that substantially all of the defect in the patient's soft tissue is closed. This can be accomplished, for example, by fastening the prosthesis using one or more layers of suturing. For example, when performing abdominal repairs, both the first and second portions may be attached to the same layer of the abdominal wall, e.g., the fascia. Alternatively, the first portion may be attached to the peritoneum. Advantageously, however, at least one of the portions is attached to the fascia because it is a stronger layer and thus provides a stronger repair. On the other hand, the peritoneum is weaker and thus a weaker repair would be effected were both the first and second portions attached thereto. Those skilled in the art will recognize other methods of attaching a prosthesis of this invention.

When repairing an incisional hernia, the prosthesis is anchored into place according to standard surgical procedures. It is sutured to a margin of healthy fascial tissue, and the size of the prosthesis is determined by the size of the defect. Advantageously, the patient is given antibiotics perioperatively, and a drain is left in place in the subcutaneous tissue for about 48 hours. The drain is then removed using standard surgical procedures. Further, the patient advantageously wears an abdominal binder, i.e., an elastic girdle, for 7-10 days following surgery.

The prosthesis of this invention has a further benefit in that it can minimize complications that can accompany soft tissue repairs. Specifically, the use of the prosthesis of this invention in a tension-free closure may be associated with less pain and less incidence of postoperative fluid accumulation (seroma). There also may be benefit in the increased tensile strength of the repair.

The invention will be described in further detail with reference to the accompanying Figures. It is to be understood that these Figures are for illustration only, and do not limit of the scope of the invention.

FIG. 1 is a view in cross-section of one embodiment of a prosthesis in accordance with this invention. The first and second portions, 10 and 12, respectively, are of essentially the same dimensions, and are of any shape or size suitable to the soft tissue defect, as discussed above. The first and second portions are arranged in substantially two layers, and are substantially entirely joined together along the interface 14. The joining may be accomplished by any known method, as discussed above. Advantageously, the portions may be joined using hemoclips (not shown).

Figure 2:
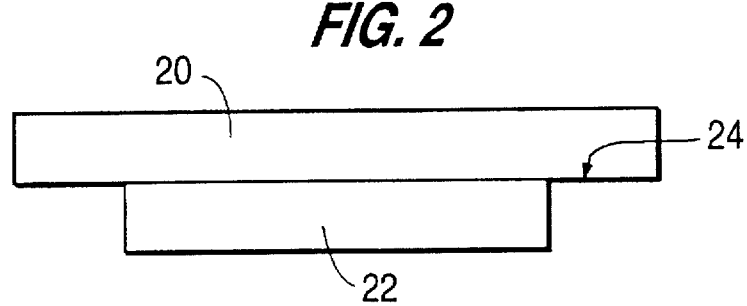
FIG. 2 is a side view in cross-section of another embodiment of a prosthesis in accordance with this invention.

FIG. 2 illustrates a view in cross-section of another embodiment of a prosthesis in accordance with this invention. The second portion 20 is larger in dimensions than the first portion 22. The two portions are of any shape or size suitable to the soft tissue defect, as discussed above. The first and second portions are arranged in substantially two layers and are joined along the interface 24 by any known means, as discussed above.

Figure 3:
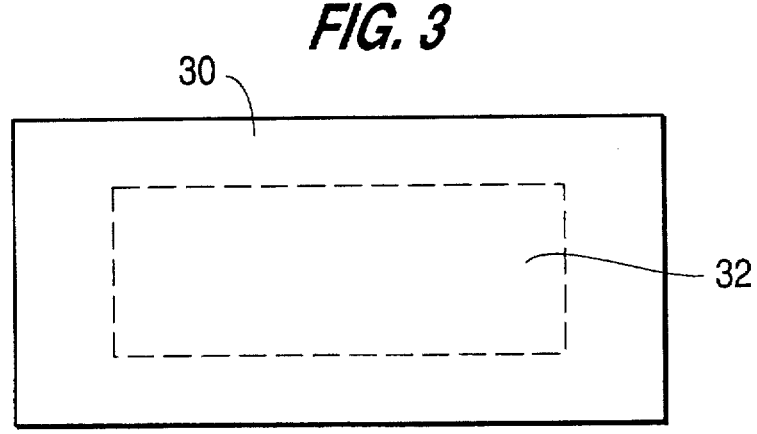
FIG. 3 is a top view of another embodiment of a prosthesis in accordance with this invention, in which the dotted lines represent the boundaries of a first portion which is located below the second portion.

FIG. 3 illustrates another embodiment of this invention. In this embodiment, the second portion 30 is larger than the first portion 32 in several dimensions, and the portions are arranged such that the perimeter of the second portion extends beyond the perimeter of the first portion in substantially all directions. The first and second portions are illustrated as rectangular but may be of any suitable size and shape, and the two portions may optionally be joined together by any known means. This embodiment advantageously provides a large surface for fascial replacement.

Figure 4:
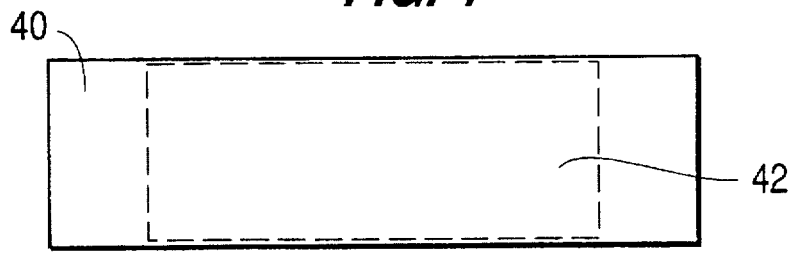
FIG. 4 is a top view of another embodiment of a prosthesis in accordance with this invention, in which the dotted lines represent the boundaries of the first portion which is located below the second portion.

FIG. 4 illustrates another embodiment of this invention. In this embodiment, the second portion 40 is larger than the first portion 42 in substantially only one dimension, and the portions are arranged such that the perimeter of the second portion extends beyond the perimeter of the first portion in fewer than all directions. The two portions optionally may be joined together by any known means, as discussed above.

Figure 5:
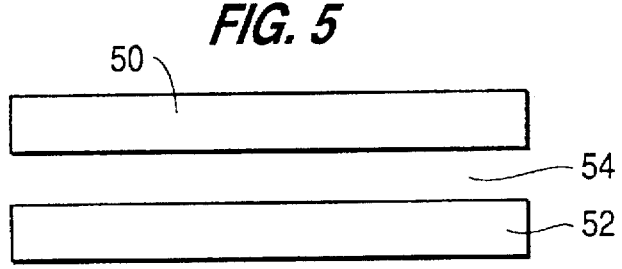
FIG. 5 is a view in cross-section of another embodiment of a prosthesis in accordance with this invention.

FIG. 5 illustrates a view in cross-section of a further embodiment of the present invention. The first portion 50 and the second portion 52 are arranged in layers, but they are not joined together, and a space 54 is present between the first and second portions.

Figure 6:
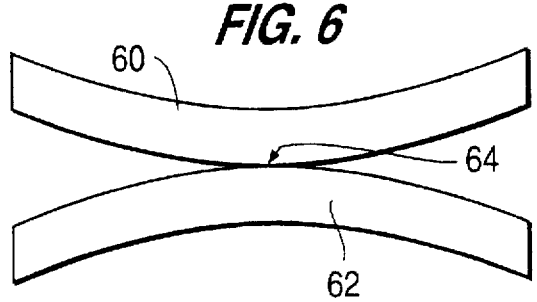
FIG. 6 is a view in cross-section of another embodiment of a prosthesis in accordance with this invention.

FIG. 6 illustrates a view in cross-section of another embodiment of the present invention. The first portion 60 and the second portion 62 are joined partially along the interface 64 by any known method, as discussed above.

Figure 7:
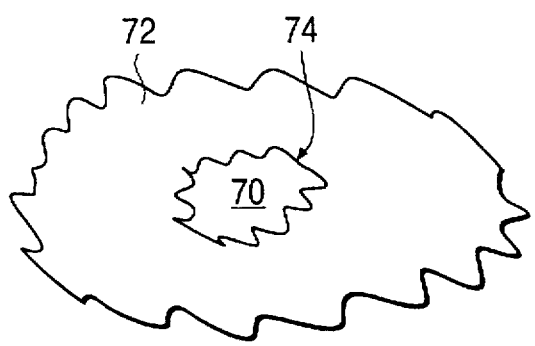
FIG. 7 is a top view of yet another embodiment of a prosthesis in accordance with this invention.

FIG. 7 illustrates a top view of a further embodiment of the present invention. In this embodiment the first portion 70 and the second portion 72 are arranged to form substantially a single layer, wherein the second portion substantially surrounds the first portion. The portions may be of any size or shape suitable to the soft tissue defect. The portions optionally may be joined along the interface 74 by any known means of joining, as discussed above.

Figure 8:
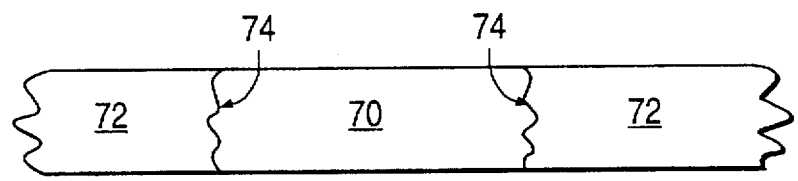
FIG. 8 is a side view in cross-section of the prosthesis illustrated in FIG. 7.

FIG. 8 illustrates a side view in cross-section of the embodiment shown in FIG. 7. The first and second portions 70 and 72 are joined along the interface 74.

Figure 9:
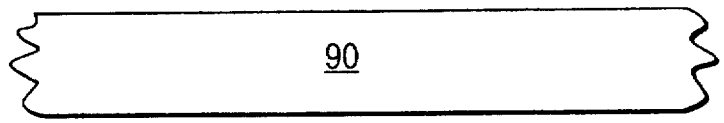
FIG. 9 is a view in cross-section of another embodiment of a prosthesis in accordance with this invention.

FIG. 9 illustrates a side view in cross-section of another embodiment of the present invention. The first and second portions are integrally formed as a single layer 90. Thus, the single layer comprises two different materials, each providing the different features discussed above.

In the figures which are referenced in the following discussion, anatomical elements appearing in more than one figure are indicated by the same reference numerals in each figure.

As mentioned above, the prosthesis of the present invention can be utilized in the repair of hernias, and, in particular, in the repair of incisional hernias.

FIG. 10 illustrates the normal anatomy of the abdominal wall. The abdominal wall consists of skin 100, subcutaneous fat 102, fascia 104, muscle 106, and a thin lining 108 called the peritoneum. Of these layers, it is the firm layer of fascia 104, a thin fibrous tissue, that provides strength to the abdominal wall, maintains the integrity of the abdominal wall and is able to hold sutures for repair of hernias.

FIG. 11 illustrates the alteration in the abdominal wall that occurs when a hernia is present. There is a defect present in the fascial layer 104 that allows for protrusion or entrapment of abdominal content. In this case, the fascia is separated, and the peritoneum 108 protrudes through the separation, forming a "hernia sac."

In the repair of hernias, the first and second portions advantageously are arranged such that the first material covers the contents of the abdominal cavity and serves as a replacement for the peritoneal surface, and the second material allows for further incorporation into the host's tissue and/or increases the structural integrity of the prosthesis to limit the effects of bulging, curling and wrinkling. The prosthesis is implanted into the patient using standard surgical techniques such that substantially all of the defect in the patient's fascia is closed.

FIG. 12 illustrates one embodiment of this invention in the repair of a hernia. In this embodiment, a prosthesis of this invention is surgically implanted such that the first portion 120 covers the fascial defect 122 and the second portion 124 is located above the first portion, and is exposed substantially only to the host's subcutaneous fat layer 102. The two portions are fastened to the muscle fascia 104 by means of sutures 126 and 128, such that substantially all of the defect is closed.

In this arrangement, the first portion 120 covers substantially all of the opening and prevents the underlying viscera from being incorporated into the second portion 124. The second portion 124 provides additional structural integrity to the prosthesis and/or facilitates incorporation of the prosthesis into the host tissue.

FIG. 13 illustrates another embodiment of the present invention in the repair of a hernia. In this embodiment, a prosthesis comprising first and second portions 130 and 132, respectively, that are partially joined is surgically implanted using suture fixation to two different abdominal layers, namely, the fascia 104 and the peritoneum 108. In this embodiment, the second portion 132 is sutured via sutures 134 and 135 to the fascia 104 and the first portion 130 is sutured via sutures 136 and 137 to the peritoneum 108. In this embodiment, a portion of the second portion 132 is exposed to muscle 106. If the second portion comprises a material that will substantially incorporate into the host tissue, such incorporation will be into the strong muscle layer 106, and will lend strong, durable fixation of the prosthesis into the host tissue. While the peritoneum 108 is not strong enough to hold a prosthesis in place on its own, the combination of suturing the second portion 132 to the fascia 104 and the first portion 130 to the peritoneum 108 provides extra strength and a safeguard in case either the peritoneum or the fascia loses its ability to hold sutures.

When attaching one portion to the peritoneum and another to the fascia, it may be preferred that the two portions be at least partially joined. This structure may provide a stronger repair and minimize the possibility of fluid build-up in the space between the first and second portions. Further, the portion attached to the peritoneum, if unattached to the other portion, could migrate if the attachment to the peritoneum would fail.

However, prostheses in which the first and second portions are not joined also may be advantageous and clearly such prostheses are contemplated. In fact, it has been observed that, in one instance in a prosthesis wherein the first portion comprised expanded PTFE and the second portion comprised polypropylene mesh and wherein the two portions were not joined together, the first and second portions adhered to each other after a few months.

Figure 14:
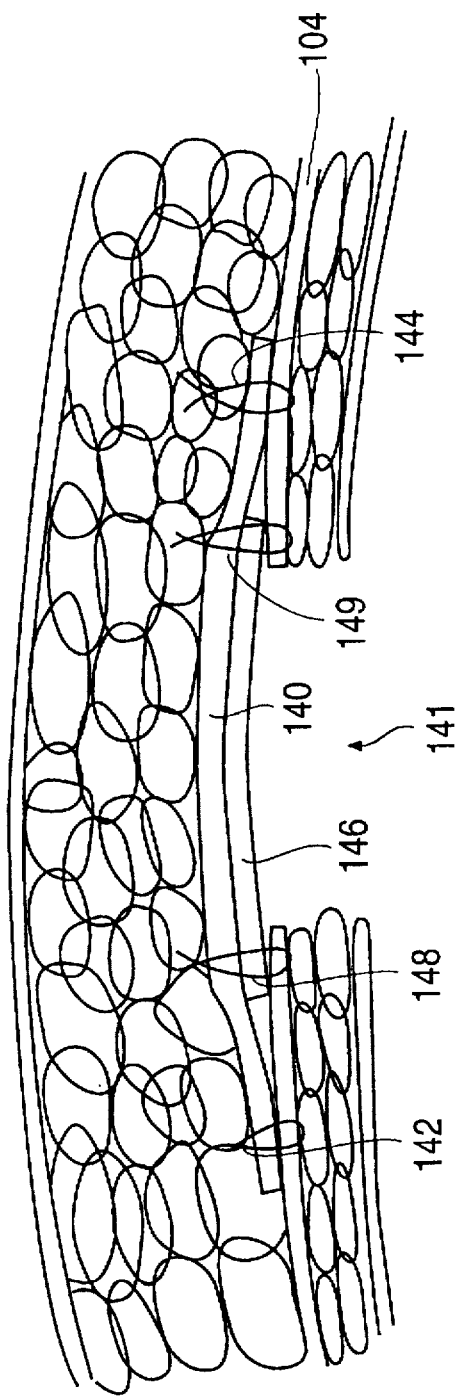
FIG. 14 is a view in cross-section of an abdominal wall that has been repaired using a prosthesis of this invention, wherein the second portion is larger in area than the first portion, and wherein the second portion is separately sutured to the underlying fascia away from the hernia defect.

FIG. 14 illustrates another embodiment of this invention, in which a prosthesis of this invention is used to repair a hernia. The prosthesis used is similar to those illustrated in FIGS. 2–4, where the second portion is larger than the first portion. As shown, the second 140 portion extends beyond the fascial defect 141 and is sutured via sutures 142 and 144 to the underlying fascia 104 separately from the first portion 146 and away from the fascial defect. The first portion 146 is sutured to the fascia 104 via sutures 148 and 149. Suturing the second portion 140 away from the fascial defect, i.e., to a stronger part of the fascia 104, provides a more durable, more secure implant than suturing the second portion 140 near the defective fascia.

Using a prosthesis similar to that illustrated in FIG. 3 in this embodiment may have an additional advantage. Most recurring hernias occur at the suture line of the original repair. Since the prosthesis of this embodiment extends well beyond the fascial defect and is sutured to the fascia away from the defect to a stronger part of the fascia, this embodiment may reduce the risk of developing additional hernias lateral to the prosthesis.

Figure 17:
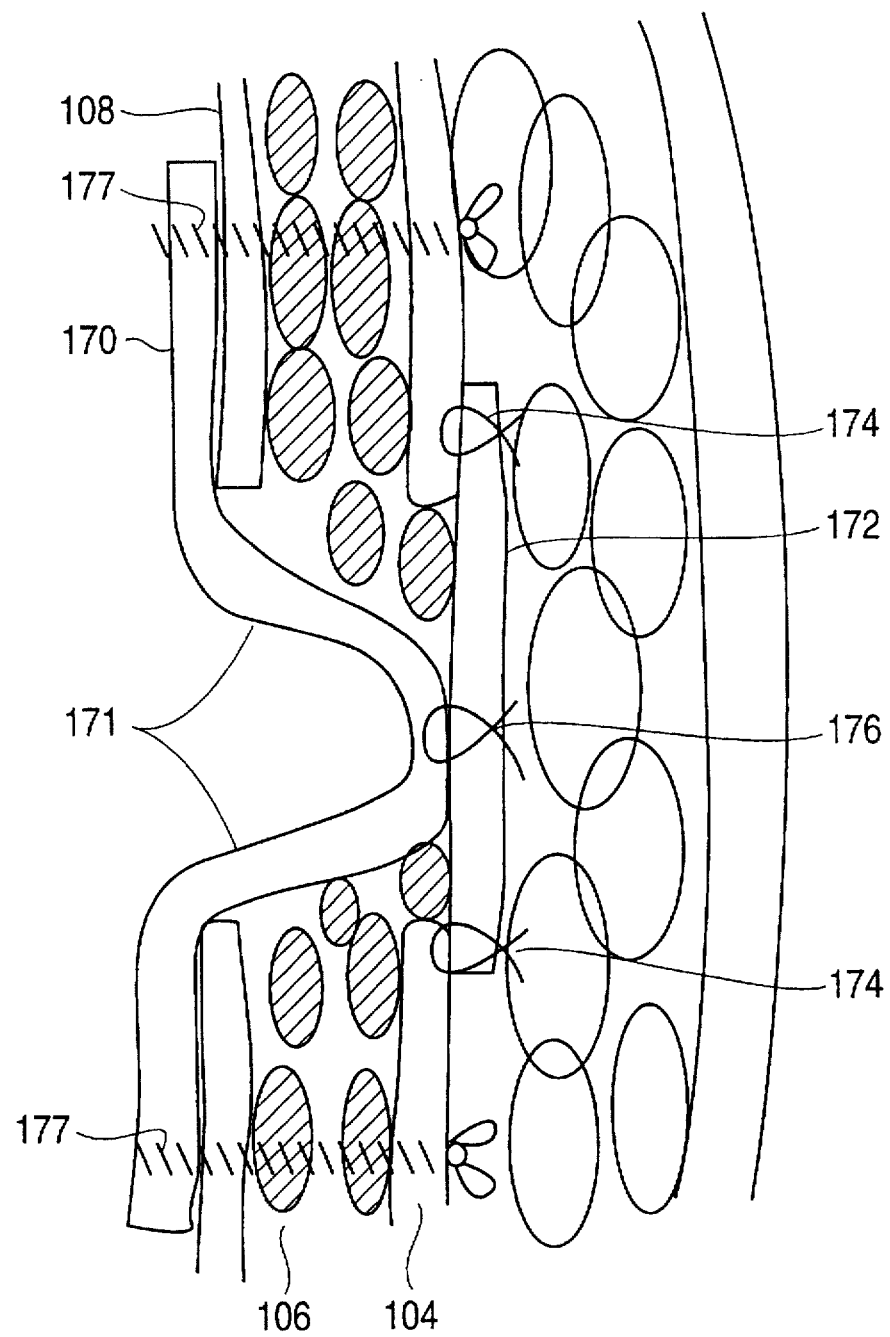
FIG. 17 is a view in cross-section of an abdominal wall that has been repaired using a prosthesis of this invention, wherein the first portion is sized to extend beyond the defect, and wherein the first portion is sutured through the peritoneum to the fascia, and the second portion is sutured to the fascia.

FIG. 17 illustrates another embodiment of the present invention in the repair of a hernia. In this embodiment, the first portion 170 is sized so that it may be implanted to overlap the peritoneum 108 and extend beyond the fascial defect 171. The first portion may be larger than the second portion. As shown, the first portion is attached via sutures 177 through the peritoneum 108 to the fascia 104. The sutures may be, for example absorbable-through-and-through mattress sutures. The second portion 172 is attached to the fascia 104 via sutures 174.

This embodiment offers several advantages. First, because the first portion is larger than the fascial defect, and is implanted so that it overlaps the peritoneum, the first potion can absorb much of the outward pressure that exists along the herniated region. This relieves pressure from the second portion, and lessens the disruption along the interface between the second portion and the fascia.

Attaching the first portion through the peritoneum to the fascia provides extra strength when compared to the embodiment where the first portion is attached to the peritoneum alone. Furthermore, suturing the first portion to the peritoneum and fascia away from the defect, i.e., to a stronger part of the fascia, provides a more durable and more secure attachment of the prosthetic device. Also, because a portion of the second portion 172 is exposed to muscle 106, if the second portion comprises a material that will substantially incorporate into the host tissue, such incorporation will be into the strong muscle layer. This will further enhance the strength and fixation of the prosthesis into the host tissue.

As discussed above, it may be preferred that the two portions be at least partially joined, for example, with sutures 176. However, prostheses in which the first and second portions are not joined also may be advantageous and clearly such prostheses are contemplated.

Figure 18:
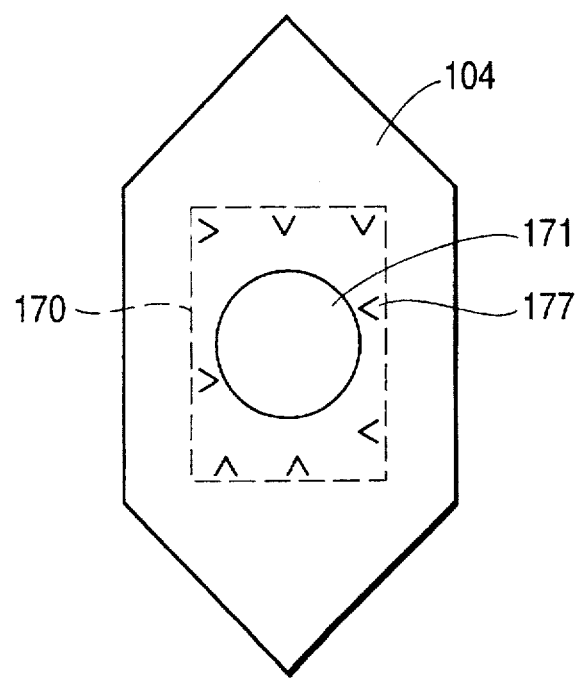
FIGS. 18 is a top view of the abdominal wall repair illustrated in FIG. 17, wherein the dotted line represents the first portion.

FIGS. 18 illustrates a top view of the embodiment of FIG. 17. The second portion is not shown. The dotted line represents the first portion 170 which is attached through the peritoneum to the fascia 104 via sutures 177, and overlaps the defect 171.

Figure 19:
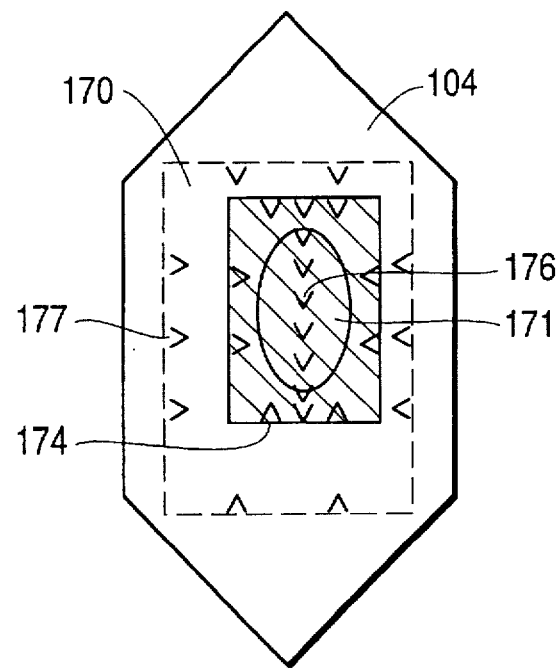
FIG. 19 is a top view of the abdominal wall repair illustrated in FIG. 17, wherein the dotted line represents the first portion and the shaded area represents the second portion.

FIG. 19 illustrates a top view of the embodiment of FIG. 17 with both the first portion 170 and second portion 172 illustrated. The second portion may be partially joined to the first portion, for example, via sutures 176. The first portion 170, represented by the dotted line, is attached through the peritoneum to the fascia 104 away from the defect 171, while the second portion 172, represented by the shaded area, is attached to the fascia closer to the defect.

The prosthesis of the present invention is suited to hernias of any size. Typically, hernias will range in size from about 3 cm to about 20 cm or more at the widest point. The first and second portions are sized according to the size of the hernia, and preferably will be sized to at least substantially completely cover the soft tissue defect. Each of the first and second portions may be sized to extend beyond the defect in one or more directions, and the portions may be of the same or different dimensions, and may have the same or different areas. Accordingly, each of the first and second portions may be sized from about 3 cm to about 20 cm or more at the widest point.

EXAMPLES

The following examples are illustrative only, and are not to be construed as limiting the scope of the invention.

A prosthesis comprising a first portion comprised of expanded PTFE and a second portion comprised of polypropylene mesh was used in the repair of incisional hernias in thirteen patients. The patients ranged in age from thirty-two to seventy-five years. There were five men and eight women. The hernia defects ranged in size from five to twenty centimeters. Four of the patients were obese.

The patients included:
- a thirty-seven-year-old female who developed a hernia in a lower midline C-section incision;
- a seventy-five-year-old-female who developed a hernia following closure of a temporary colostomy site in the right upper quadrant of the abdomen; and
- a thirty-eight-year-old female who developed a recurrent hernia in a gall bladder incision following a repair with expanded PTFE used alone.

Various techniques were used to anchor the first and second portions of the prosthesis in place. In some instances the first and second portions were sutured in place separately, while in other instances the first and second portions were secured together by sutures or hemoclips before being sewn onto the abdominal wall defect. In one patient there was sufficient peritoneal tissue to allow separate peritoneal closure; in all other patients the prosthesis was used to replace both the peritoneal and fascial surfaces.

Routine perioperative care included the administration of broad spectrum antibiotics pre-operatively and for at least forty-eight hours post-operatively. Closed suction drainage was used for forty-eight hours and patients were fitted with an abdominal binder to be worn in the initial post-operative period.

There were no wound infections complicating the immediate post-operative period in any patient, but one patient, a sixty-seven-year-old male, developed a dehiscence of his skin closure which resulted in exposure of the prosthesis and allowed a late infection of the wound. Although no persistent sinus tract or obvious sepsis occurred, the prosthesis was later removed. No adhesions of the underlying viscera to the prosthesis were noted at the time of removal.

In one particular case, a prosthesis similar to that illustrated in FIG. 5 was surgically implanted to repair a hernia in an obese, sixty-year-old female. This patient developed post-operative pain lateral to the anchored prosthesis. A seroma was drained under ultrasound guidance and although the seroma did not recur, the patient continued to have localized pain and subsequently manifested a hernia lateral to the placement of the prosthesis.

The remaining patients in this series have all had unremarkable post-operative courses and are continuing to be monitored. The short term results demonstrate that the composite prosthesis can be successfully used in the repair of abdominal wall defects.

Figure 15:
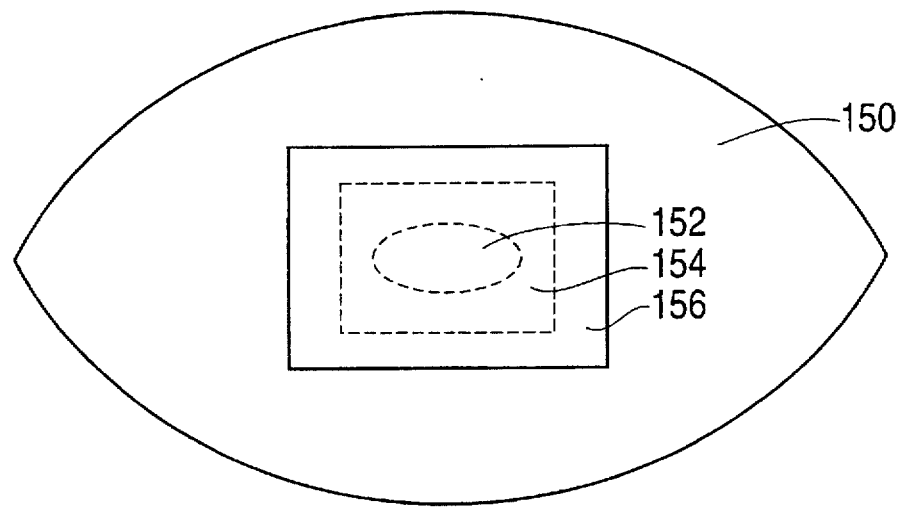
FIG. 15 is an illustration of an abdominal wall repair (skin and subcutaneous fat layers not shown) using a prosthesis of this invention, wherein in the figure the dotted lines represent the boundaries of a first portion that is located below a second portion, and a hernia which is located below the first portion.

To prevent the development of recurring hernias lateral to the prosthesis, the embodiment illustrated in FIG. 3 has been used in the repair of hernias. FIG. 15 is a top view of an abdominal wall 150 with a hernia 152 which was repaired with a prosthesis of this embodiment. (The skin and subcutaneous fat layers are not shown.) In this repair, the expanded PTFE portion 154 was sized and shaped to fit the size and shape of the hernia 152 and the polypropylene portion 156 was larger than the expanded PTFE portion and extended beyond the expanded PTFE portion in essentially all directions. The polypropylene portion and the expanded PTFE portion were not joined together prior to being implanted in the patient. The prosthesis was implanted as described above in reference to FIG. 14.

Figure 16:
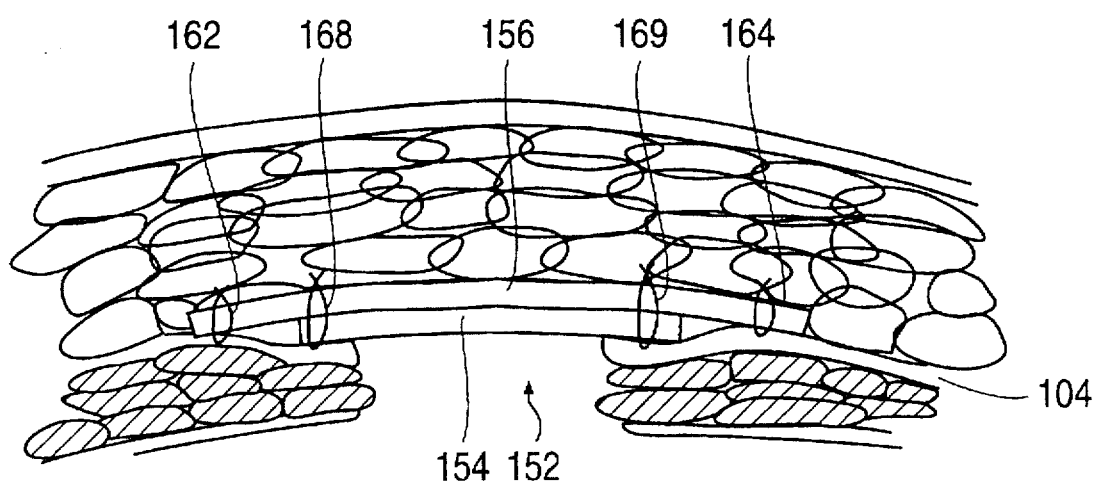
FIG. 16 is a view in cross-section of the abdominal wall repair illustrated in FIG. 15.

FIG. 16 illustrates a view in cross-section of the abdominal wall repair illustrated in FIG. 15. The polypropylene portion 156 extended beyond the hernia 152 and was attached via sutures 162 and 164 to the fascia 104, separately from the expanded PTFE portion 154 and away from the hernia 152. The expanded PTFE portion 154 was sutured to the fascia 104 via sutures 168 and 169. This configuration provided a large surface of polypropylene for fascial replacement and attached the polypropylene portion to a stronger part of the fascia, minimizing the risk of developing additional hernias lateral to the prosthesis.

The following is a prophetic example. The prosthesis illustrated in FIGS. 17, 18 and 19 is used to perform an abdominal wall repair. The first portion 170 comprises PTFE, and is sized to extend beyond the hernia defect 171. It is attached by absorbable-through-and through-mattress sutures through the peritoneum 108 to the fascia 104 away from the hernia defect. The second portion 172 comprises polypropylene, and is attached to the fascia 104 by sutures 174. The first and second portions are joined by a central row of sutures 176. This embodiment allows the first portion to absorb much of the pressure along the herniated region, thereby lessening pressure and disruption along the interface of the fascia and the second portion.

It will be apparent to those skilled in the art that various modifications and variations can be made to the compositions and process of this invention. Thus, it is intended that the present invention cover the modifications and variations of this invention provided they come within the scope of the appended claims and their equivalents.

What is claimed is:

1. A process for treating a soft tissue defect of a patient comprising the step of surgically implanting adjacent the soft tissue defect a prosthesis comprising:
   a first portion comprising a first material which substantially does not incorporate into the host tissue, wherein said fist portion is sized to extend beyond said defect, and
   a second portion comprising a second material selected from the group of materials consisting of a material which substantially incorporates into the host tissue, a material which increases the structural integrity of the prosthesis, and a material which does both.

2. The process of claim 1, wherein said second portion substantially completely covers said soft tissue defect.

3. The process of claim 2, wherein said first portion is larger in area than said second portion.

4. The process of claim 1, wherein said second portion is attached to said first portion.

5. The process of claim 1, wherein said soft tissue defect is a hernia.

6. The process of claim 5, wherein said second portion is surgically attached to the fascia and said first portion is surgically attached to the fascia through the peritoneum.

7. The process of claim 6, wherein said first portion is attached to the fascia through the peritoneum by absorbable-through-and-through mattress sutures.

8. The process of claim 5, wherein said hernia is an incisional hernia.

9. The process of claim 5, wherein said hernia is of a size of from about 3 cm to about 20 cm or more in width.

10. The process of claim 9, wherein said second portion substantially completely covers said soft tissue defect.

11. The process of claim 10, wherein said first portion is larger in area than said second portion.

12. The process of claim 9, wherein said first portion is of about the same area as said second portion.

* * * * *